United States Patent

Steube et al.

[11] Patent Number: 5,322,514
[45] Date of Patent: Jun. 21, 1994

[54] NEEDLE ASSEMBLY WITH DETACHABLE WING

[75] Inventors: Gregory A. Steube, St. Charles, Mo.; Ronald W. Ausherman, Orange City, Fla.

[73] Assignee: Sherwood Medical Company, St. Louis, Mo.

[21] Appl. No.: 932,149

[22] Filed: Aug. 19, 1992

[51] Int. Cl.$^5$ .............................................. A61M 5/14
[52] U.S. Cl. ..................................... 604/177; 604/192; 604/263; 604/264
[58] Field of Search ................ 604/177, 174, 188, 192, 604/162, 263, 264

[56] References Cited

U.S. PATENT DOCUMENTS

| | | | |
|---|---|---|---|
| D. 217,795 | 6/1970 | Spaven et al. | D83/12 |
| 2,857,913 | 10/1958 | Miskel | 128/221 |
| 2,922,420 | 1/1960 | Cheng | 128/221 |
| 2,952,256 | 9/1960 | Meader et al. | 128/221 |
| 3,782,381 | 1/1974 | Winnie | 128/214.4 |
| 3,856,009 | 12/1974 | Winnie | 128/214.4 |
| 3,921,633 | 11/1975 | Tischlinger | 128/218 R |
| 4,020,835 | 5/1977 | Nordstrom et al. | 128/214.4 |
| 4,068,661 | 1/1978 | Hennings | 128/215 |
| 4,209,015 | 6/1980 | Wicks | 128/214.4 |
| 4,233,974 | 11/1980 | Desecki et al. | 128/215 |
| 4,345,596 | 8/1982 | Young | 128/214 R |
| 4,445,893 | 5/1984 | Bodicky | 604/165 |
| 4,518,383 | 5/1985 | Evans | 604/51 |
| 4,565,544 | 1/1988 | Muller et al. | 604/164 |
| 4,609,370 | 9/1986 | Morrison | 604/165 |
| 4,629,452 | 12/1986 | Wahlberg et al. | 604/177 |
| 4,772,266 | 9/1988 | Groshong | 604/164 |
| 4,828,549 | 5/1989 | Kvalo | 604/164 |
| 4,834,708 | 5/1989 | Pillari | 604/165 |
| 4,863,432 | 9/1989 | Kvalo | 604/177 |
| 4,869,718 | 9/1989 | Brader | 604/164 |
| 4,880,412 | 11/1989 | Weiss | 604/165 |
| 4,919,653 | 4/1990 | Martinez et al. | 604/117 |
| 4,940,458 | 7/1990 | Cohn | 604/51 |
| 4,973,312 | 11/1990 | Andrew | 604/158 |
| 4,973,313 | 11/1990 | Katsaros et al. | 604/165 |
| 4,986,814 | 1/1991 | Burney et al. | 604/164 |
| 5,085,639 | 2/1991 | Ryan | 604/177 |
| 5,108,376 | 4/1992 | Benaldo | 604/177 |
| 5,112,311 | 5/1992 | Utterberg et al. | 604/177 |

FOREIGN PATENT DOCUMENTS

| | | | |
|---|---|---|---|
| 2929886 | 1/1981 | Fed. Rep. of Germany | 604/177 |
| 92/11885 | 7/1992 | PCT Int'l Appl. | 604/177 |

Primary Examiner—Gene Mancene
Assistant Examiner—Todd E. Manahan
Attorney, Agent, or Firm—Andrew J. Beck; Montgomery W. Smith; Curtis D. Kinghorn

[57] ABSTRACT

An epidural or anesthesia needle assembly having a "wing" selectively attachable to the needle hub is disclosed. The "wing" is made of a sturdy but resilient material. The "wing" has a tang for placing in a corresponding slot in the needle hub to ensure the correct orientation of the "wing" with the bevel tip of the cannula. In addition, the tang allows the "wing" to be pushed along the elongated axis of the cannula with improved efficiency so that the "wing" does not become inadvertently detached from the needle hub. In the preferred embodiment, the "wing" includes a protective sheath mount enclosure shaped in contour to the protective sheath mount located at the most distal end of the needle hub. The protective sheath mount enclosure forms a lock around the protective sheath mount. The contour shape of the protective sheath mount enclosure encloses the protective sheath mount so that as the "wing" is moved either proximally or distally, the resilient material of the "wing" around the protective sheath mount enclosure moves into locking contact with the protective sheath mount.

24 Claims, 6 Drawing Sheets

NEEDLE ASSEMBLY WITH DETACHABLE WING

BACKGROUND OF THE INVENTION

1. Field of the Invention

This invention relates to needle assemblies and more specifically to assemblies, such as epidural and anesthesia needle assemblies, that require finger sensitivity and finger control in placement of the cannula in a patient's body.

2. Description of Related Art

Many needle assemblies are known for placing cannulae in the body. In some cases, an incision is cut into the body and a cannula placed therethrough. In others, a cannula is inserted directly into the body. Thereafter, a catheter is placed through the cannula into the body. In many cases it is desirable to use finger control to insert and position the cannula in the body. Often it is desirable to have a great amount of finger sensitivity when placing the cannula in the body to precisely position the cannula. In addition, it is often desirable to have means to readily move the cannula into and out of the body along the elongated axis of the needle assembly.

To satisfy these requirements, needle assemblies having finger manipulation members or "wings" that extend away from the elongated axis of the needle assembly at approximately right angles have been developed. In one method of use, these "wings" allow the physician to grasp the needle assembly with two fingers on the "wing" while placing the thumb on the proximal or non-patient contacting end of the needle assembly. The needle assembly is held by the proximal force put on the wing by the physician's fingers counter balanced by the distal force put on the proximal end of the needle assembly. In this way, distal directed pressure can be applied to the needle assembly by the thumb to push the cannula into the body or the cannula may be moved proximally out of the patient's body by the proximal movement of fingers pulling on the "wings". In addition, the "wings" allow the physician to turn the needle assembly around its elongated axis by rotating his wrist in order to more precisely position the cannula and its typically beveled distal end.

In another method of use, the physician grasps the "wings" with both hands by holding each "wing" between the corresponding thumb and index finger of each hand. In this method, one hand holds the "wing" extending from one side of the needle assembly while the other hand holds the "wing" extending from the other side of the needle assembly. The physician may then either push or pull on the "wings" thereby moving the cannula into or out of the patient's body, respectively. In this method of use, the physician may turn the needle assembly, and consequently the cannula, around its elongated axis by raising or lowering one "wing" relative to the other.

Figure 1:
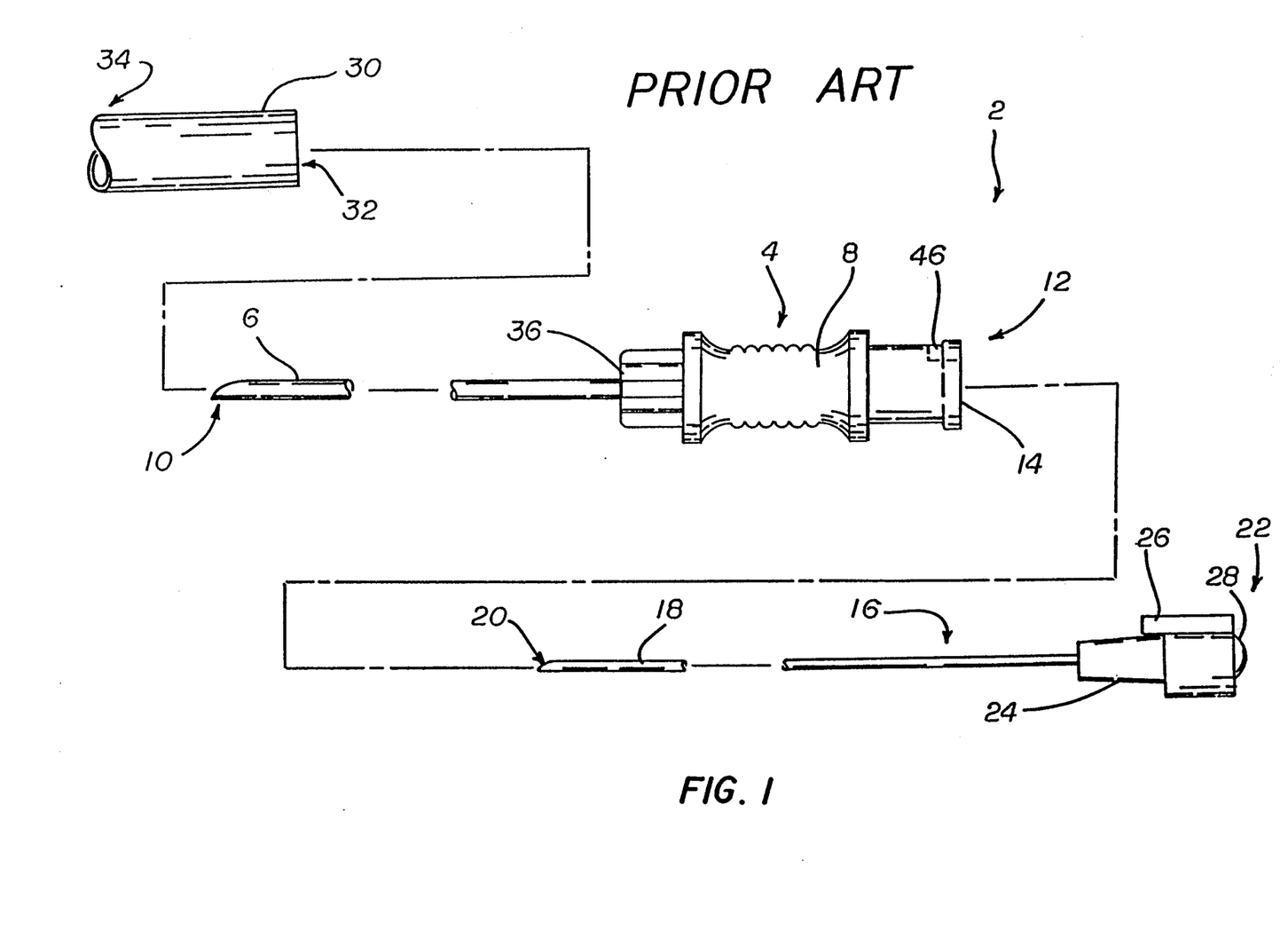
FIG. 1 is a side exploded view of a typical assembly device.

A standard epidural needle assembly is shown in FIG. 1 generally labeled 2. The needle assembly 2 includes a cannula assembly 4 comprising an elongated hollow cannula 6 attached to a needle hub 8. The patient contacting or distal end 10 of cannula 6 typically has a bevel to produce a sharpened end. The needle hub 8, located at proximal end 12 of cannula assembly 4, is finger manipulated by the physician so that cannula 6 may be inserted into the patient's body. A bore 14 extends through needle hub 8 from the proximal end 12 of cannula assembly 4 to the inner bore of cannula 6. A slot 46 extends into needle hub 8 from its proximal end 12.

Slot 46 is located along the outer surface of needle hub 8 parallel to bore 14.

Needle assembly 2 also includes a stylet assembly 16. Stylet assembly 16 includes a stylet 18 and a stylet hub 24. Stylet 18 is typically a solid metal rod. The distal end 20 of stylet 18 generally has a bevel corresponding in angle to the angle of the bevel of the distal end 10 of cannula 6.

Stylet hub 24 is located at the proximal end 22 of stylet assembly 16. Stylet hub 24 includes a tang 26 directed toward the distal end 20 of stylet assembly 16. In operation, as will be explained hereafter, when stylet 18 is placed through bore 14 into cannula 6 so that the distal end 20 of stylet 18 is aligned with the distal end 10 of cannula 8, tang 26 will intermesh with slot 46 in needle hub 8 to precisely orient the beveled distal end 20 of stylet 18 with the beveled distal end 10 of cannula 6.

When stylet 18 is fully inserted into cannula 6 and the beveled distal end 20 of stylet 18 and the beveled distal end 10 of cannula 6 are aligned by tang 26 intermeshing with slot 46, a flat surface is presented across the beveled distal ends 10, 20 of cannula 6 and stylet 18, respectively. This provides a substantially closed surface at the distal end 10 of cannula 6 to prevent coring of the patient while inserting the cannula 6 into the patient.

Stylet hub 24 also includes a thumb piece 28 located on the proximal end 22 of stylet assembly 16. Thumb piece 28 allows the physician to move stylet assembly 16 distally by pushing on thumb piece 28 with the physician's thumb.

A protective sheath 30, typically comprising a rigid cylindrical plastic tube, is provided to encase cannula 6 when not in use and prevent inadvertent contact with the sharp beveled distal end 10. Protective sheath 30 has a proximal end 32 that contacts a protective sheath mount 36 located at the distal end of needle hub 8. When protective sheath 30 is in position over cannula 6 so that the proximal end 32 is in contact with protective sheath mount 36, protective sheath 30 is sufficiently long so that the distal end 34 of protective sheath 30 extends beyond the distal end 10 of cannula 6. In this way, persons and objects are protected from unwanted contact with the sharp distal end 10 of cannula 6 by the covering of the rigid protective sheath 30. Protective sheath 30 is removed prior to the physician inserting cannula 6 into the patient's body.

Many epidural or anesthesia needle systems 2 have a wing 38 mounted on needle hub 8. Typically, wing 38 is a thin, substantially planar device that extends away from the main axis of needle hub 8 at substantially a right angle near the distal end of needle hub 8.

Many epidural or anesthesia needle assemblies 2 attach wings 38 to needle hub 8 permanently; in the case of metal needle assemblies 2, the wings 38 are soldered to the needle assembly 2. However, it is often desirable to be able to selectively remove wing 38. Therefore, wings 38 that may be removed from needle hub 8 are known.

One typical way to attach wing 38 to needle hub 8 is to form a slot in needle hub 8, substantially aligned with the plane of wing 38. A corresponding tab is formed on wing 38 to slide into and be constrained by the slot. However, a problem with this system for attaching wing 38 to needle hub 8 is that either proximal or distal pressure on wing 38 by the physician causes wing 38 to deform. As a result of wing 38 deforming, the tabs on wing 38 move out of constraining contact with the slot in needle hub 8, thereby detaching wing 38 from needle hub 8. Besides creating an annoying condition for the doctor, the condition is also potentially unsafe because the physician has temporarily lost control of the cannula 6 in the patient's body. Therefore it is highly desirable to provide an epidural or anesthesia needle assembly 2 with detachable wings 38 where the wings 38 may be securely fastened to the needle hub 8, yet easily removed if desired.

As stated, a problem with some prior art epidural needle assemblies 2 having wings 38 is that the wings 38 are integrally connected to the cannula. Consequently, in applications where it is desired that the epidural needle assemblies 2 be used without wings 38, a separate version of the epidural needle assembly 2 must be produced; one having and one not having wings 38. This leads to production duplication and inventory and storage problems. As a result, it is desirable to make an epidural needle assembly that may or may not be used with "wings" as desired.

SUMMARY OF THE INVENTION

An epidural or anesthesia needle assembly having a "wing" selectively attachable to the needle hub is provided. The "wing" is made of a sturdy but resilient material. The "wing" has a tang for placing in a corresponding slot in the needle hub to ensure the correct orientation of the "wing" with the bevel tip of the cannula. In addition, the tang allows the "wing" to be pushed along the elongated axis of the cannula with improved efficiency so that the "wing" does not become inadvertently detached from the needle hub.

In the preferred embodiment, the "wing" includes a protective sheath mount enclosure shaped in contour to the protective sheath mount located at the most distal end of the needle hub. The protective sheath mount enclosure forms a lock around the protective sheath mount. The contour shape of the protective sheath mount enclosure encloses the protective sheath mount so that as the "wing" is moved either proximally or distally, the resilient material of the "wing" around the protective sheath mount enclosure moves into locking contact with the protective sheath mount.

It is therefore an object of the instant invention to provide an epidural/anesthesia needle assembly having a "wing" that allows a physician to easily move the cannula into the patient's body.

It is another object of the instant invention to provide an epidural/anesthesia needle assembly having a detachable "wing".

It is a further object of the instant invention to provide an epidural/anesthesia needle assembly having a detachable "wing" which wing is locked in position on the needle hub during use.

It is a further object of the instant invention to provide an epidural/anesthesia needle assembly with a "wing" that is aligned with the a particular orientation of the cannula.

It is another object of the instant invention to provide an epidural/anesthesia needle assembly having a "wing" that shows the orientation of the beveled distal end of the cannula by the "wings" orientation around the central axis of the epidural/anesthesia needle assembly.

It is another object of the instant invention to provide an epidural/anesthesia needle assembly with a "wing" that efficiently transfers pressure from the physician's thumb and fingers along the elongated axis of the cannula from the "wing" to the needle hub and consequently to the cannula.

These and other objects of the instant invention will be clear from the description contained herein and more particularly with reference to the following detailed description of the invention and the accompanying drawings. In the drawings, like elements are referred to by like reference numerals.

DETAILED DESCRIPTION OF THE INVENTION

Figure 2:
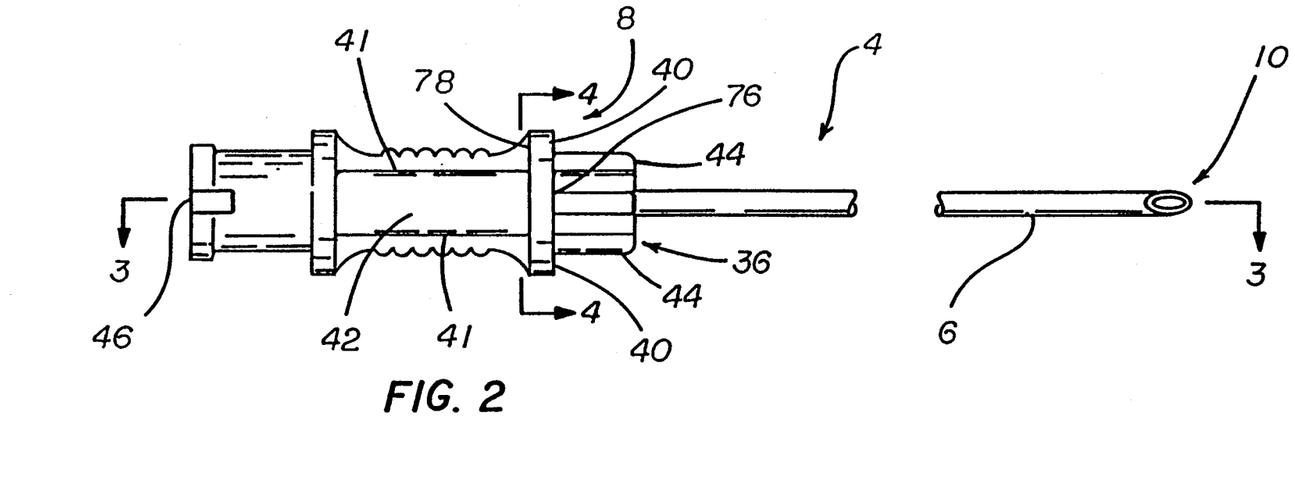
FIG. 2 is a plan view of a cannula assembly.

FIG. 2 shows a top plan view of a cannula assembly 4. The cannula assembly 4 shown in FIG. 2 may be very effectively used without attaching a wing 38, if desired.

Cannula assembly 4 includes a needle hub 8 and cannula 6 as described above. A pair of opposed wing mounts 40 are provided integrally formed with and extending away from needle hub 8 near the distal end of needle hub 8. Wing mounts 40 extend away from needle hub 8 at approximately right angles to the axis of bore 14. Wing mounts 40 have a substantially planar distal surface 76 and a parallel substantially planar proximal surface 78, spaced a small distance apart to form a narrow, substantially planar member extending away from needle hub 8 at a right angle to the axis of bore 14. Wing mounts 40 interact with wings 38 as explained hereafter to position wings 38 on needle hub 8.

Figure 3:
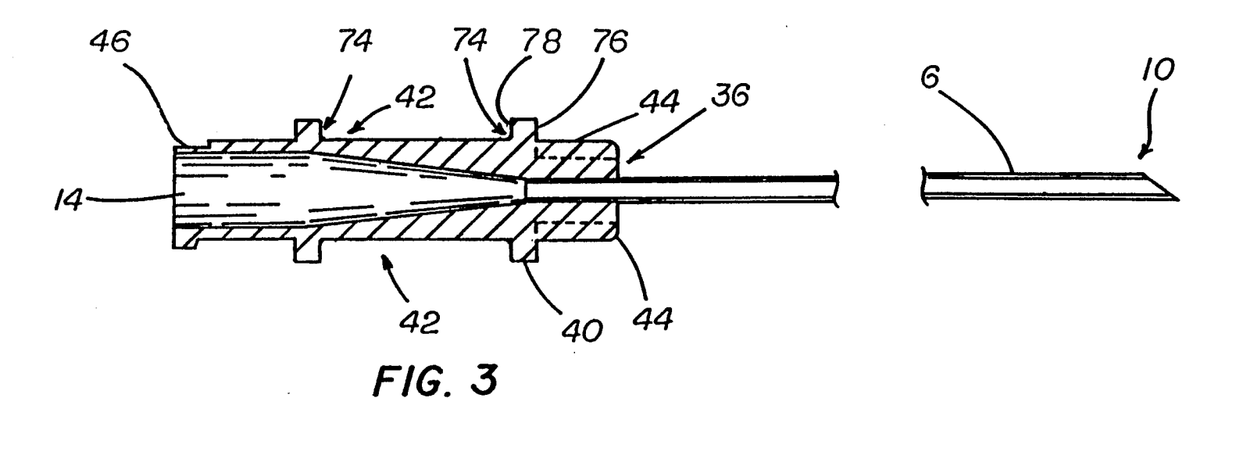
FIG. 3 is a cross-sectional view of the cannula assembly of FIG. 2, taken along line labelled 3—3 in FIG. 2.
Figure 4:
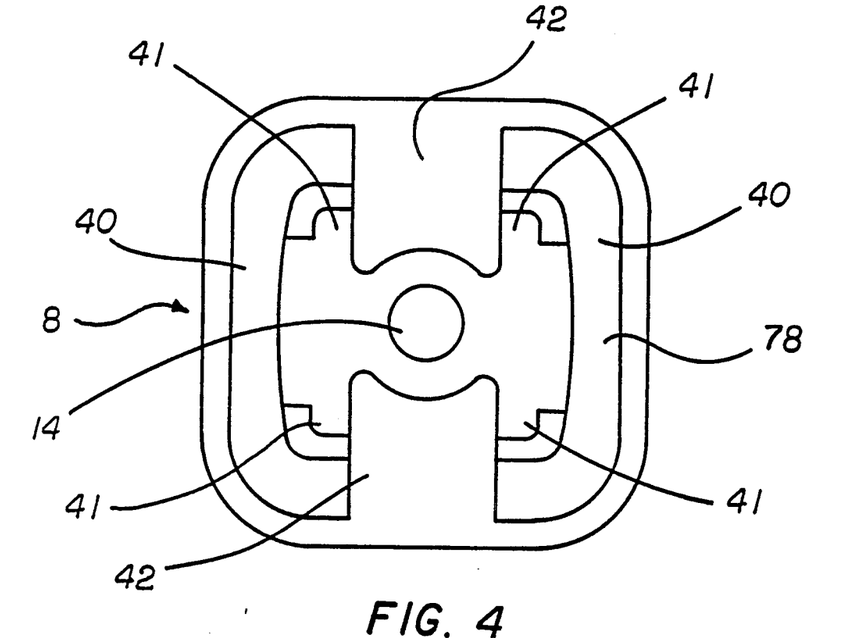
FIG. 4 is a cross-section view through the needle hub of the cannula assembly of FIG. 2 looking toward the distal end of the cannula assembly along the line labelled 4—4 in FIG. 2.

As shown in FIGS. 2, 3 and 4, needle hub 8 includes a slot 42 extending into needle hub 8 toward bore 14 formed between two parallel spaced apart slot side pieces 41. Slot 42 is preferably aligned with a particular orientation of the bevel of the distal end 10 of cannula 6. In one embodiment, two slots 42 may be placed on opposite sides of needle hub 8 as shown in FIG. 3. Slot 42 has a distal end 74 defined by the proximal surface 78 of wing mount 40.

Figure 9:
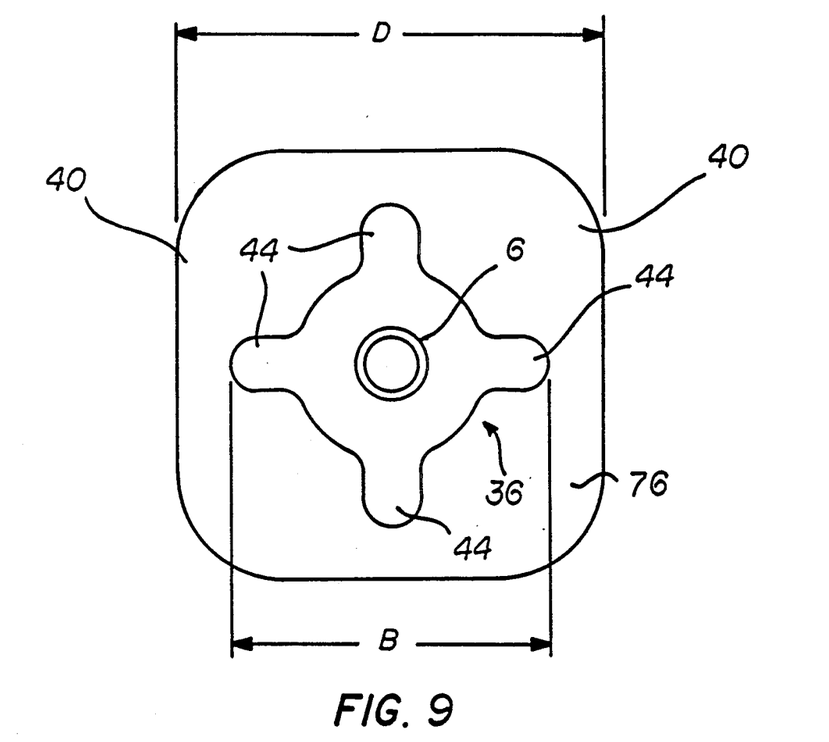
FIG. 9 is a plan view of the cannula assembly as viewed from its most distal end.

A protective sheath mount 36 is provided at the ultimate distal end of needle hub 8. As shown in more detail in FIG. 9, protective sheath mount 36 includes a series of flat protruding tabs 44 extending away from the axis of cannula 6 along rays from the axis of cannula 6 The planes of tabs 44 are parallel to the axis of cannula 6. Protective sheath 30 has an inside diameter approximately equal to the outer diameter B of tabs 44. Protective sheath 30 is placed over and in contact with tabs 44 so that frictional contact between tabs 44 and the inside of protective sheath 30 securely holds protective sheath 30 in place over cannula 6 to provide a guard for the distal end 10 of cannula 6.

As best shown in FIGS. 2 and 3, needle hub 8 also includes a tang slot 46 for receiving the tang 26 of stylet hub 24 when stylet 18 is placed within bore 14 and cannula 6. As stated above, the interaction between tang 26 and tang slot 46 precisely positions stylet 18, and particularly the beveled distal end 20 of stylet 18, within cannula 6 so that a substantially flat surface is presented at the distal end 10 of cannula 6 to prevent coring of a patient.

In operation, stylet 18 is placed within the hollow cannula 6 through the proximal end 12 of bore 14. Stylet hub 24 is rotated until tang 26 is aligned with tang slot 46. Stylet hub 24 is moved distally until tang 26 is engaged with tang slot 46. At this time, the beveled distal end 22 of stylet 18 will be aligned with the beveled distal end 10 of cannula 6 to present a closed surface across the distal end 10 of cannula 6.

Figure 5:
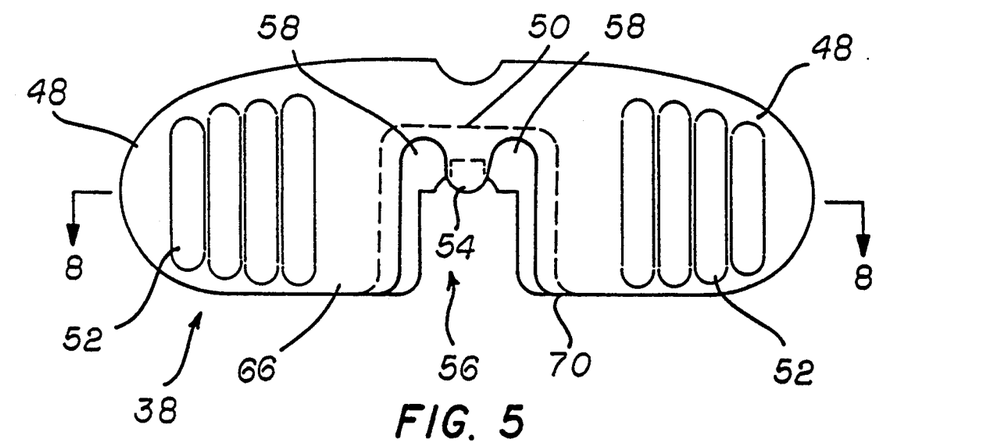
FIG. 5 is a plan view of the proximal side of the wing of the instant invention.
Figure 8:
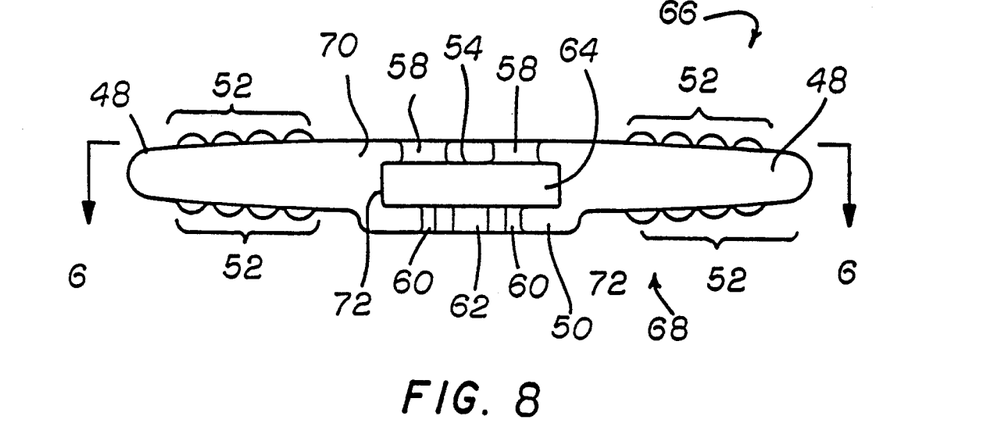
FIG. 8 is a side view of the wing of FIGS. 4 and 5 along the line labeled 8—8 in FIGS. 5 and 6.

FIG. 5 shows a plan view of the proximal side 66 of wing 38 of the instant invention. As can be seen, wing 38 includes two opposed side pieces 48 extending outwardly from a central body 50. As can be seen in FIG. 8, side pieces 48 and body 50 are relatively narrow in cross-section compared to their width. Side pieces 48 preferably include a series of finger pads 52 on both its proximal and distal sides 66,68 to provide frictional contact between the finger of the physician and the surface of the proximal and distal sides 66,68 of side pieces 48.

A needle hub bore 56 extends through the proximal side 66 and distal side 68 of wing 38. Needle hub bore 56 includes a wing mount slot 64 located between the proximal and distal sides 66,68 of wing 38. Needle hub bore 56 extends into proximal and distal sides 66,68 from one edge 70 of wing 38 so that an opening is presented into wing 38 along edge 70.

Referring to FIG. 5, a wing tang 54 extends into needle hub bore 56 from the proximal side 66 of wing 38 opposite edge 70. Wing tang 54 is preferably shaped in substantial contour to the cross-sectional shape of slot 42 in needle hub 8 shown in FIG. 4 just proximal to wing mounts 40. Needle hub bore 56 includes a pair of side piece slots 58 on either side of wing tang 54 corresponding in contour to side pieces 41 which define slot 42.

Figure 6:
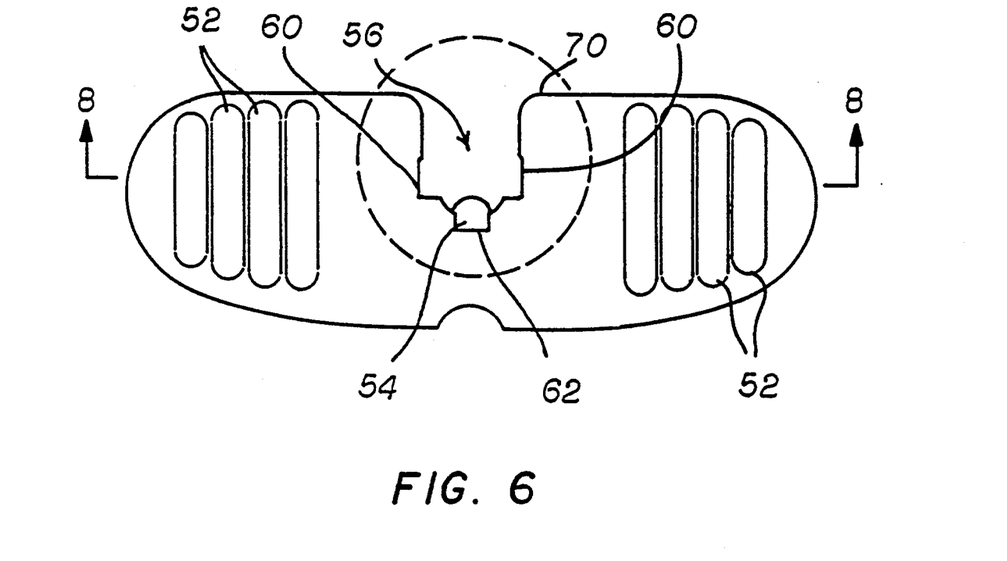
FIG. 6 is a plan view of the distal side of the wing of FIG. 5.

The distal side 68 of wing 38 is shown in FIG. 6. As can be seen, side pieces 48 also have finger pads 52 on the distal side 68 as well as on the proximal side 66 shown in FIG. 5. The details of the structure of needle hub bore 56 through the distal side 68 are shown in more detail in FIG. 7.

Figure 7:
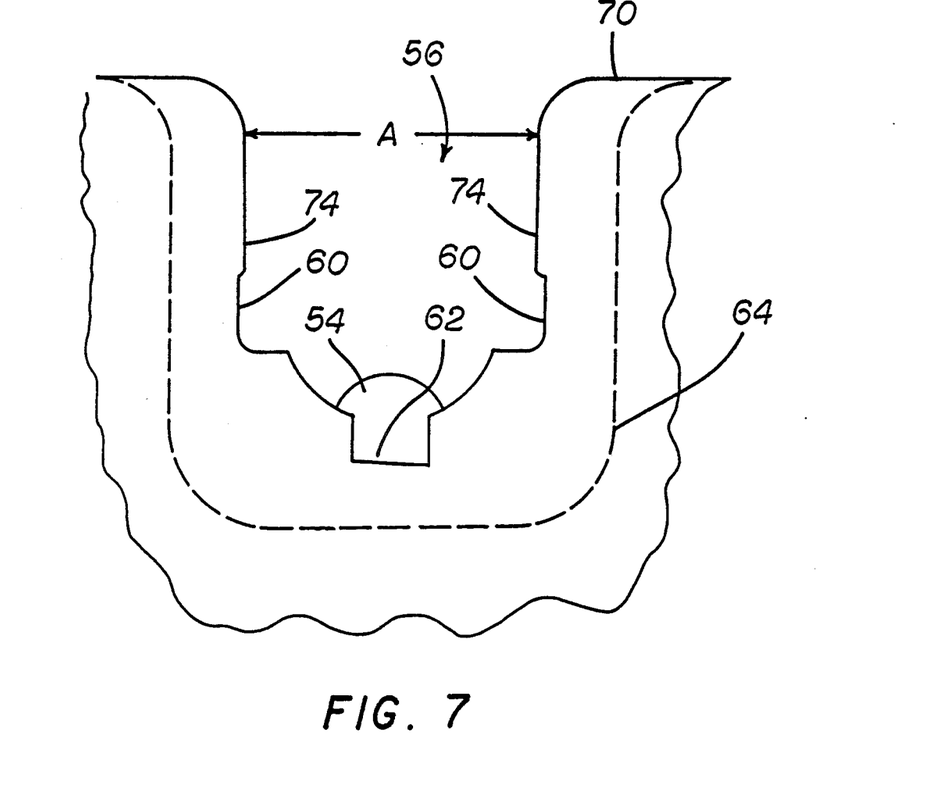
FIG. 7 is an enlarged view of the area encircled with a dashed line in FIG. 6.

Referring to FIG. 7, needle hub bore 56 on the distal side 68 includes three Gab slots 60,62. The side tab slots 60 are opposed to each other while end tab slot 62 is located at approximately a 90° angle to either of side tab slots 60 and opposite edge 70. Tab slots 60,62 are formed to correspond in contour to tabs 44 on protective sheath mount 36. The distance across side slots 60 is approximately the distance B across tabs 44. Sides 74 defining needle hub bore 56 near edge 70 on distal side 68 are spaced apart a distance A that is less than the furthest distance B across opposed tabs 44.

As best seen in FIG. 8, a wing mount slot 64 is formed between the material of body 50 defining needle hub bore 56 on both of the proximal and distal sides 66,68 of wing 38. Wing mount slot 64 has a width equal to the distance D across wing mount 40. In use, wing 38 is slid onto wing mount 40 so that wing mounts 40 come into frictional contact with the side edges 72 of wing mount slot 64.

In FIG. 7, the outline of wing mount slot 64 of needle hub bore 56 is shown in dotted line. Wing tang 54 is shown extending into needle hub bore 56 from proximal side 66. Wing tang 54 can be seen because wing tang 54 extends farther into needle hub bore 56 than does the material of the distal side 58 around side and end tab slots 60,62.

Figure 10:
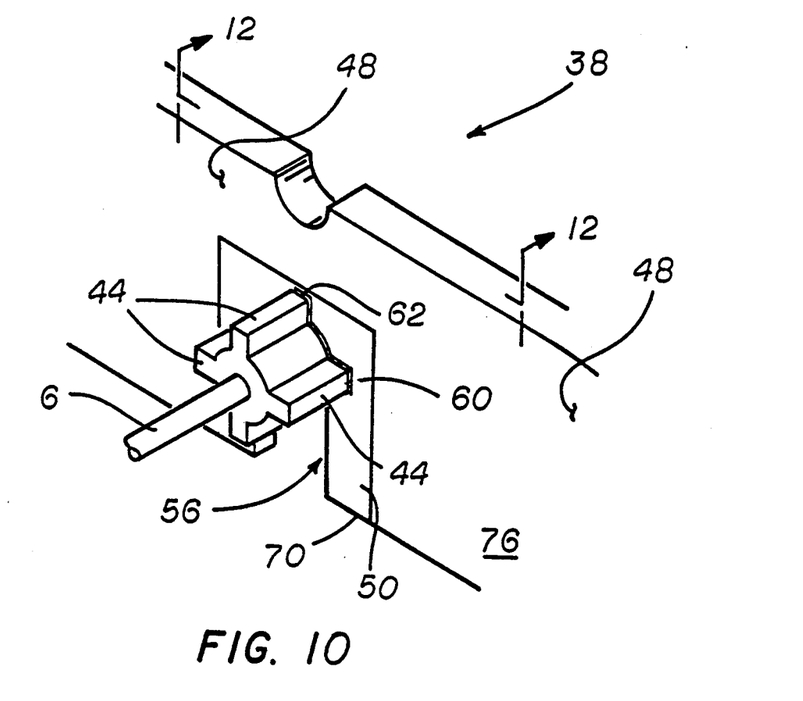
FIG. 10 is a perspective view of the distal side of the wing of the instant invention in contact with the protective sheath mount.

As wing 38 is moved onto wing mounts 40, tabs 44 contact side edges 72 of the distal side 68 of needle hub bore 56. Because the distance B across tabs 44 is larger than the distance A between side edges 72 of needle hub bore 56, the resilient material of body 50 forming side edges 72 must bend to allow tabs 44 to move across side edges 72. Also, while wing 38 is moved onto wing mounts 40, a tab 44, at 90° to the tabs 44 contacting side edges 72, will be aligned with and move toward end tab slot 62.

As wing 38 is moved further onto wing mounts 40, eventually opposed tabs 44 will move past side edges 72 into side tab slots 60. Simultaneously the tab 44 at the 90° angle to the tabs 44 that moved into side tab slots 60 will be securely positioned within end tab slot 62. At this time, the resilient material of the distal side 68 of body 50 around side tab slots 60 will move into position to encase tabs 44 located within side and end tab slots 60,62.

Figure 12:
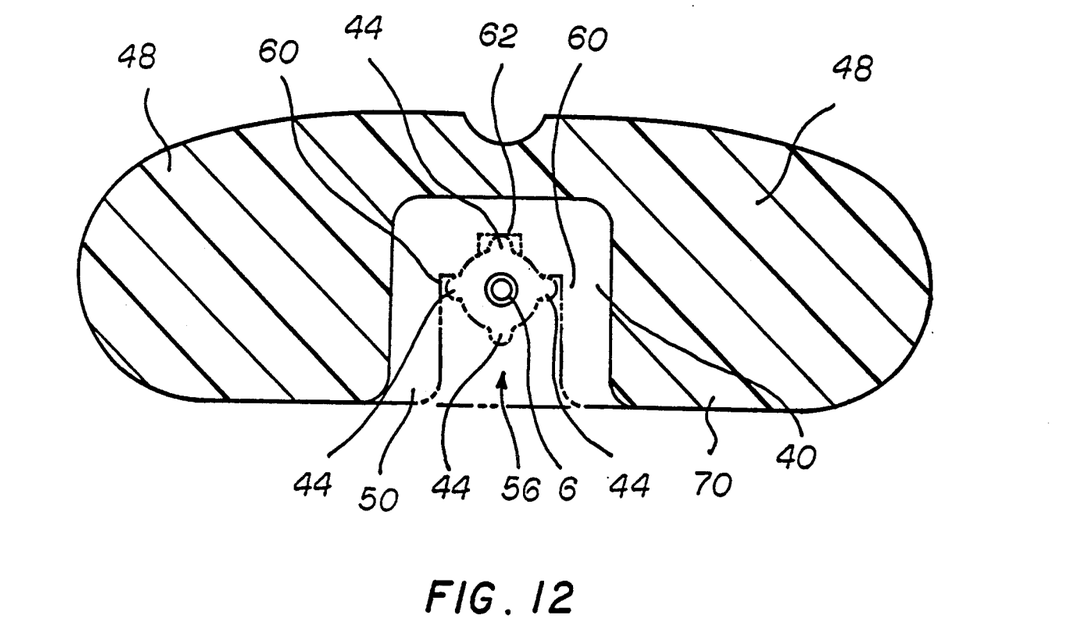
FIG. 12 is a cross-sectional view of wing of the instant invention attached to a needle hub with the view taken through the plane of the wing.

Also, as wing 38 moves onto wing mounts 40, wing tang 54 moves into slot 42 of needle hub 8. As opposed tabs 44 move into secure contact within tab slots 60, wing tab 54 moves into secure contact between side pieces 41. Also, wing tab 54 moves into contact with the most distal end 74 of slot 42 in needle hub 8 so that wing mounts 40 are securely positioned within wing mount slot 64. At this time, the material of the proximal side 66 of body 50 including wing tang 54 will be on one side and the material of the distal side 68 of body 50 will be on the other side of wing mount 40 thereby enclosing wing mount 40 within wing mount slot 64.

The physician then grasps the needle assembly 2 with his fingers on the proximal side 66 of wing 38 and his thumb on the thumb piece 28 of stylet hub 24. The cannula assembly 4 is moved into the desired position in the patient's body by manipulating the cannula assembly 4 through the use of the wing 38 and thumb piece 28. After cannula 6 is in the desired position, stylet 18 is removed. In the case of an epidural needle assembly, a small catheter is then placed through bore 14 into the central lumen of cannula 6 and then into the patient's body. Thereafter, cannula 6 is removed from the patient's body leaving the catheter extending from the opening in the patient's body created by the removal of the cannula 6.

In operation, the doctor may also push on the proximal side 66 of side pieces 48 with distal pressure from his thumbs or fingers thereby pushing wing tang 54 and the material around the proximal side 66 of needle hub bore 56 into contact with distal end 74 of slot 42 and the proximal surface 78 of wing mounts 40. This pushes needle hub 8 and cannula 6 distally into the patient's body. Sufficient pressure on the proximal side 66 of side pieces 48 will cause wing 38 to deform distally toward cannula 6. This forces the material of body 50 around the distal side 68 of needle hub bore 56 onto and into tighter frictional contact with the edges of tabs 44 of protective sheath mount 36. This contact between the material of body 50 around the distal side 68 of needle hub bore 56 and tabs 44 of protective sheath mount 36 causes wing 38 to resist deforming. This helps to keep wing 38 from moving out of contact with wing mounts 40 and detaching from needle hub 8 as the physician applies pressure in the distal direction.

Although a particular shape has been shown for the side pieces 41 and slot 42 of needle hub 8 and tabs 44 on protective sheath mount 36, along with corresponding contour shapes of the proximal side 66 and wing tang 54 and the distal side 68, respectively, of wing 38, these particular shapes are not necessary to the operation of the invention. The key feature being that the distal side 68 of needle hub bore 56 is in contour shape and comes in contact with and encloses and encases whatever shape protective sheath mount 36 may be presented, while wing tang 54 is in contour shape with and is securely positioned in whatever shape slot 42 is presented and tang 54 abuts the distal end 74 of slot 42 while the proximal side 66 of body 50 encloses and encases side pieces 41.

Figure 11:
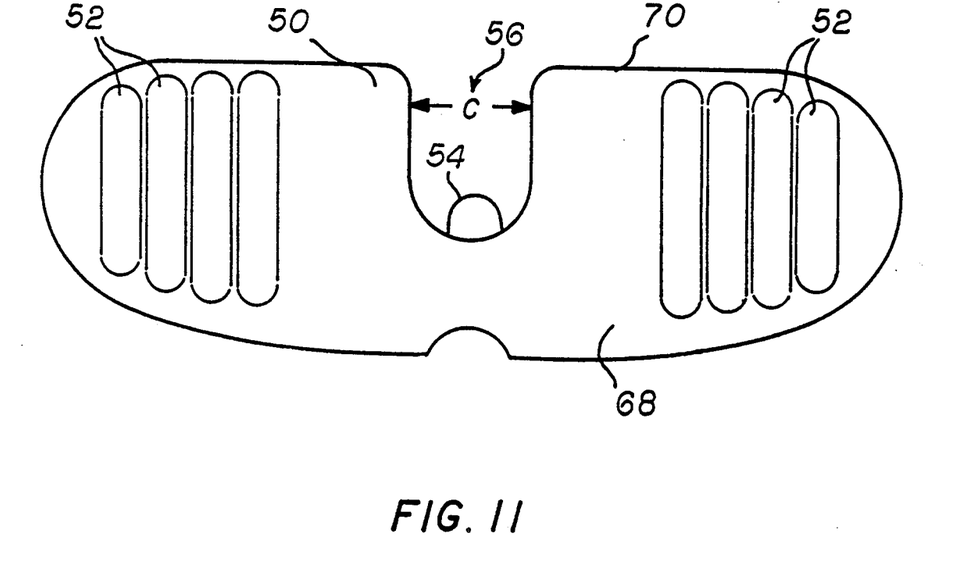
FIG. 11 is a plan view of the distal side of the wing of an alternate embodiment of the instant invention.

FIG. 11 shows a variation of the wing 38. The structure of side pieces 48 is identical to that described above. In the body 50, the proximal side 66 of needle hub bore 56, including wing tang 54, is exactly as that described above. However, the structure of body 50 on the distal side 68 of needle hub bore 56 includes a roughly elongated hemispherical shape opposite edge 70. In this embodiment, there are no side or end tab slots 60,62. Instead, the width C of needle hub bore 56 in distal side 68 is approximately equal to or slightly less than the width B across opposed tabs 44. In all other ways, the embodiment shown in FIG. 11 is identical to the preferred embodiment disclosed herein.

This embodiment allows wing tang 54 to contact the distal end 74 of slot 42 to move the cannula 6 distally into the patient. Although not believed to be as effective in holding wing 38 in position on wing mounts 40 as the preferred embodiment, it is believed that the structure of body 50 defining needle bore 56 at distal side 68 will still cause the material of body 50 to contact opposed tabs 44 in a compressed fashion to frictionally lock wing 38 onto protective sheath mount 36.

Wing 38 is preferably made of a resilient polymer material such as polyvinylchloride (PVC), polyurethane or silicone. Wing 38 should be stiff enough to be able to attach to wing mounts 40 and to allow the physician to put pressure on needle hub 8 through wing mounts 40 without substantially deforming wing 38. However, as described above, wing 38 should have sufficient flexibility to allow the side edges 72 of the distal side 68 of body 50 to deform to allow tabs 44 to move between side edges 72 and also allow the material of body 50 around side and end tab slots 60,62 to move into secure contact with tabs 44 and the space between tabs 44 on protective sheath mount 36.

Although a needle assembly has been described herein as an epidural needle assembly, the "wing" of the instant invention may be used as well on other needle assemblies such as anesthesia needles, IV catheter needles and spinal needles, to name but a few of the possibilities.

The instant invention has been described in connection with a specific embodiment. However, the description contained herein has been given for the purpose of illustration and not for the purpose of limitation. Changes may be made to the structure disclosed and still be within the scope of the invention. Obvious changes and modifications will occur to those skilled in the art.

We claim:

1. A medical device comprising:
   a) a needle assembly having a needle hub attached to a cannula, said cannula located on the distal end of said needle assembly and said needle hub located on the proximal end of said cannula, said needle hub having opposed protrusions extending away from said needle hub;
   b) a finger manipulation member having at least one axis of finger contact;
   c) means for removably connecting said finger manipulation member to said opposed protrusions so that said axis of finger contact, when said finger manipulation member is connected to said opposed protrusions, is substantially perpendicular to the axis of said cannula, said means for removably connecting comprising a first wall and a second wall in said finger manipulation member, said first wall spaced apart from said second wall to define a finger manipulation member slot, said first wall located distal to said second wall, said first wall spaced from said second wall by approximately the width of said opposed protrusions, said finger manipulation slot for receiving and constraining said opposed protrusions therein, each of said walls having an edge directed in approximately the same direction, said first and said second walls each having an opening formed into each of said walls from each respective said edges, each of said openings in said first and second walls shaped in contour to said needle hub in the area where said first and second walls intersect said needle hub when said opposed protrusions are moved into said finger manipulation slot from the direction of said edges.

2. The device of claim 1 wherein said needle hub includes:
   a) a pair of spaced apart side pieces, positioned parallel to the axis of said cannula and defining a needle hub slot therebetween;
   b) said needle hub having a substantially flat needle hub slot end located between said side pieces to form a distal end for said needle hub slot, said needle hub slot end substantially aligned with said opposed protrusion pieces; and,
   wherein said opening in said second wall includes a tang extending into said opening in said second wall from opposite said edge of said second wall toward said edge of said second wall, said tang being substantially planar with said second wall and shaped in substantial contour to said needle hub slot, said tang contacting said needle hub slot end when said opposed protrusions are moved into said finger manipulation slot from the direction of said edges so that pressure in a distal direction on said finger manipulation member is transferred to said needle hub by the contact between said tang and said needle hub slot end.

3. An anesthesia needle assembly comprising:
a) a cannula having a distal and a proximal end, said cannula having an opening at said distal end of said cannula;
b) a needle hub attached to said cannula at said proximal end of said cannula, said needle hub having a bore extending therethrough coaxial with and aligned with said cannula, said bore in communication with said cannula, said needle hub having opposed protrusions extending away from said needle hub;
c) a finger manipulation member having at least one axis of finger contact;
d) means for removably connecting said finger manipulation member to said opposed protrusions so that said axis of finger contact, when said finger manipulation member is connected to said opposed protrusions, is substantially perpendicular to the axis of said cannula;
e) a removable stylet placed within said cannula through said bore of said needle hub, said stylet having a distal and a proximal end, said distal end of said stylet blocking said opening at said distal end of said cannula;
f) means for positioning said stylet within said cannula and said bore of said needle hub; and,
g) means for transferring pressure in a distal direction on said finger manipulation member to said needle hub, said means for transferring distal pressure comprising:
  i) a pair of spaced apart side pieces, positioned on said needle hub parallel to the axis of said cannula and defining a needle hub slot therebetween;
  ii) a substantially flat needle hub slot end located between said side pieces to form a distal end for said needle hub slot, said needle hub slot end substantially aligned with the proximal side of said opposed protrusion pieces;
  iii) a first wall and a second wall in said finger manipulation member, said first wall spaced apart from said second wall to define a finger manipulation member slot, said first wall located distal to said second wall, said first wall spaced from said second wall by approximately the width of said opposed protrusions, said finger manipulation slot for receiving and constraining said opposed protrusions therein, each of said walls having an edge directed in approximately the same direction, said first and said second walls each having an opening formed into each of said walls from each respective said edges, each of said openings in said first and second walls shaped in contour to said needle hub in the area where said first and second walls intersect said needle hub when said opposed protrusions are moved into said finger manipulation slot from the direction of said edges; and,
  iv) a tang extending into said opening in said second wall from opposite said edge of said second wall toward said edge of said second wall, said tang being substantially planar with said second wall and shaped in substantial contour to said needle hub slot, said tang contacting said needle hub slot end when said opposed protrusions are moved into said finger manipulation slot from the direction of said edges so that pressure in the distal direction on said finger manipulation member is transferred to said needle hub by the contact between said tang and said needle hub slot end.

4. A medical device comprising:
a) a needle assembly having a needle hub attached to a cannula, said cannula located on the distal end of said needle assembly and said needle hub located on the proximal end of said cannula, said needle hub having opposed protrusions extending away from said needle hub;
b) a protective sheath removably encasing said cannula to prevent inadvertent contact with said cannula;
c) a protective sheath mount, attached to said needle hub, for mounting said protective sheath around said cannula;
d) a finger manipulation member having at least one axis of finger contact, said finger manipulating member including a protective sheath mount enclosure contoured in shape to said protective sheath mount;
e) means for removably connecting said finger manipulation member to said opposed protrusions so that said axis of finger contact, when said finger manipulation member is connected to said opposed protrusions, is substantially perpendicular to the axis of said cannula, whereby said protective sheath mount enclosure encloses said protective sheath mount when said finger manipulating member is connected to said opposed protrusions; and,
f) means for transferring pressure in a distal direction on said finger manipulation member to said needle hub comprising:
  i) a pair of spaced apart side pieces, positioned on said needle hub parallel to the axis of said cannula and defining a needle hub slot therebetween;
  ii) a substantially flat needle hub slot end located between said side pieces to form a distal end for said needle hub slot, said needle hub slot end substantially aligned with the proximal side of said opposed protrusion pieces;
  iii) a first wall and a second wall in said finger manipulation member, said first wall spaced apart from said second wall to define a finger manipulation member slot, said first wall located distal to said second wall, said first wall spaced from said second wall by approximately the width of said opposed protrusions, said finger manipulation slot for receiving and constraining said opposed protrusions therein, each of said walls having an edge directed in approximately the same direction, said first and said second walls each having an opening formed into each of said walls from each respective said edges, each of said openings in said first and second walls shaped in contour to said needle hub in the area where said first and second walls intersect said needle hub when said opposed protrusions are moved into said finger manipulation slot from the direction of said edges; and,
  iv) a tang extending into said opening in said second wall from opposite said edge of said second wall toward said edge of said second wall, said tang being substantially planar with said second wall and shaped in substantial contour to said needle hub slot, said tang contacting said needle hub slot end when said opposed protrusions are moved into said finger manipulation slot from the direction of said edges so that pressure in the distal direction on said finger manipulation member is transferred to said needle hub by the contact between said tang and said needle hub slot end.

5. A medical device comprising:
a) a needle assembly having a needle hub attached to a cannula, said cannula located on the distal end of said needle assembly and said needle hub located on the proximal end of said cannula, said needle hub having opposed protrusions extending away from said needle hub, said needle hub including a protective sheath mount;
b) a finger manipulation member having at least one axis of finger contact, said finger manipulating member including a protective sheath mount enclosure contoured in shape to said protective sheath mount;
c) means for removably connecting said finger manipulation member to said opposed protrusions so that said axis of finger contact, when said finger manipulation member is connected to said opposed protrusions, is substantially perpendicular to the axis of said cannula; and,
d) a protective sheath removably encasing said cannula to prevent inadvertent contact with said cannula, said protective sheath mount enclosure enclosing said protective sheath mount when said finger manipulating member is connected to said opposed protrusions, said protective sheath mount for mounting said protective sheath around said cannula and including at least a first pair of opposed tabs extending away from and parallel to the axis of said cannula.

6. The device of claim 5 wherein said protective sheath mount enclosure includes at least a pair of opposed slots contoured in shape to said first pair of opposed tabs.

7. The device of claim 6 wherein said protective sheath mount includes a second pair of opposed tabs located at right angles to said first pair of opposed tabs and wherein said protective sheath mount enclosure includes an end tab contoured in shape to one tab of said second pair of opposed tabs.

8. A medical device comprising:
a) a needle assembly having a needle hub attached to a cannula, said cannula located on the distal end of said needle assembly and said needle hub located on the proximal end of said cannula, said needle hub having opposed protrusions extending away from said needle hub;
b) a finger manipulation member having at least one axis of finger contact;
c) means for removably connecting said finger manipulation member to said opposed protrusions so that said axis of finger contact, when said finger manipulation member is connected to said opposed protrusions, is substantially perpendicular to the axis of said cannula, said means for removably connecting comprising a first wall and a second wall in said finger manipulation member, said first wall spaced apart from said second wall to define a finger manipulation member slot, said first wall located distal to said second wall, said first wall spaced from said second wall by approximately the width of said opposed protrusions, said finger manipulation slot for receiving and constraining said opposed protrusions therein, each of said walls having an edge directed in approximately the same direction, said first and said second walls each having an opening formed into each of said walls from each respective said edges, each of said openings in said first and second walls shaped in contour to said needle hub in the area where said first and second walls intersect said needle hub when said opposed protrusions are moved into said finger manipulation slot from the direction of said edges.

9. The device of claim 8 wherein said needle hub includes:
a) a pair of spaced apart side pieces, positioned parallel to the axis of said cannula and defining a needle hub slot therebetween;
b) said needle hub having a substantially flat needle hub slot end located between said side pieces to form a distal end for said needle hub slot, said needle hub slot end substantially aligned with said opposed protrusion pieces; and,
wherein said opening in said second wall includes a tang extending into said opening in said second wall from opposite said edge of said second wall toward said edge of said second wall, said tang being substantially planar with said second wall and shaped in substantial contour to said needle hub slot, said tang contacting said needle hub slot end when said opposed protrusions are moved into said finger manipulation slot from the direction of said edges so that pressure in a distal direction on said finger manipulation member is transferred to said needle hub by the contact between said tang and said needle hub slot end.

10. A medical device comprising:
a) a needle assembly having a needle hub attached to a cannula, said cannula located on the distal end of said needle assembly and said needle hub located on the proximal end of said cannula, said needle hub having opposed protrusions extending away from said needle hub;
b) a finger manipulation member having at least one axis of finger contact;
c) means for removably connecting said finger manipulation member to said opposed protrusions so that said axis of finger contact, when said finger manipulation member is connected to said opposed protrusions, is substantially perpendicular to the axis of said cannula;
d) means for transferring pressure in a distal direction on said finger manipulation member to said needle hub comprising:
  i) a pair of spaced apart side pieces, positioned on said needle hub parallel to the axis of said cannula and defining a needle hub slot therebetween;
  ii) a substantially flat needle hub slot end located between said side pieces to form a distal end for said needle hub slot, said needle hub slot end substantially aligned with the proximal side of said opposed protrusion pieces;
  iii) a first wall and a second wall in said finger manipulation member, said first wall spaced apart from said second wall to define a finger manipulation member slot, said first wall located distal to said second wall, said first wall spaced from said second wall by approximately the width of said opposed protrusions, said finger manipulation slot for receiving and constraining said opposed protrusions therein, each of said walls having an edge directed in approximately the same direction, said first and second walls each having an opening formed into each of said walls from each respective said edges, each of said openings in said first and second walls shaped in contour to said needle hub in the area where said first and second walls intersect said needle hub when said opposed protrusions are moved into said finger manipulation slot from the direction of said edges; and, iv) a tang extending into said opening in said second wall from opposite said edge of said second wall toward said edge of said second wall, said tang being substantially planar with said second wall and shaped in substantial contour to said needle hub slot, said tang contacting said needle hub slot end when said opposed protrusions are moved into said finger manipulation slot from the direction of said edges so that pressure in the distal direction on said finger manipulation member is transferred to said needle hub by the contact between said tang and said needle hub slot end.

11. An anesthesia needle assembly comprising:
a) a cannula having a distal and a proximal end, said cannula having an opening at said distal end of said cannula;
b) a needle hub attached to said cannula at said proximal end of said cannula, said needle hub having a bore extending therethrough coaxial with and aligned with said cannula, said bore in communication with said cannula, said needle hub having opposed protrusions extending away from said needle hub;
c) a finger manipulation member having at least one axis of finger contact;
d) means for removably connecting said finger manipulation member to said opposed protrusions so that said axis of finger contact, when said finger manipulation member is connected to said opposed protrusions, is substantially perpendicular to the axis of said cannula;
e) a removable stylet placed within said cannula through said bore of said needle hub, said stylet having a distal and a proximal end, said distal end of said stylet blocking said opening at said distal end of said cannula;
f) means for positioning said stylet within said cannula and said bore of said needle hub; and
g) a protective sheath removably encasing said cannula to prevent inadvertent contact with said cannula;

wherein said needle hub includes a protective sheath mount for mounting said protective sheath around said cannula;

wherein said finger manipulating member includes a protective sheath mount enclosure contoured in shape to said protective sheath mount, said protective sheath mount enclosure enclosing said protective sheath mount when said finger manipulating member is connected to said opposed protrusions; and wherein said protective sheath mount includes at least a first pair of opposed tabs extending away from and parallel to the axis of said cannula.

12. The device of claim 11 wherein said protective sheath mount enclosure includes at least a pair of opposed slots contoured in shape to said first pair of opposed tabs.

13. The device of claim 12 wherein said protective sheath mount includes a second pair of opposed tabs located at right angles to said first pair of opposed tabs and wherein said protective sheath mount enclosure includes an end tab contoured in shape to one tab of said second pair of opposed tabs.

14. The device of claim 11 wherein said finger manipulating member is made of a resilient material so that when said finger manipulation member is connected to said opposed protrusions and pressure in a distal direction is placed on said finger manipulating member, said finger manipulating member deforms in the area around said protective sheath mount enclosure thereby moving said material of said finger manipulation member around said protective sheath mount enclosure into secure contact with said protective sheath mount.

15. The device of claim 11 wherein said means for removably connecting comprises a first wall and a second wall in said finger manipulation member, said first wall spaced apart from said second wall to define a finger manipulation member slot, said first wall located distal to said second wall, said first wall spaced from said second wall by approximately the width of said opposed protrusions, said finger manipulation slot for receiving and constraining said opposed protrusions therein, each of said walls having an edge directed in approximately the same direction, said first and said second walls each having an opening formed into each of said walls from each respective said edges, each of said openings in said first and second walls shaped in contour to said needle hub in the area where said first and second walls intersect said needle hub when said opposed protrusions are moved into said finger manipulation slot from the direction of said edges.

16. The device of claim 15 wherein said needle hub includes:
a) a pair of spaced apart side pieces, positioned parallel to the axis of said cannula and defining a needle hub slot therebetween;
b) said needle hub having a substantially flat needle hub slot end located between said side pieces to form a distal end for said needle hub slot, said needle hub slot end substantially aligned with said opposed protrusion pieces; and,
wherein said opening in said second wall includes a tang extending into said opening in said second wall from opposite said edge of said second wall toward said edge of said second wall, said tang being substantially planar with said second wall and shaped in substantial contour to said needle hub slot, said tang contacting said needle hub slot end when said opposed protrusions are moved into said finger manipulation slot from the direction of said edges so that pressure in a distal direction on said finger manipulation member is transferred to said needle hub by the contact between said tang and said needle hub slot end.

17. The device of claim 15 further comprising means for transferring pressure in a distal direction on said finger manipulation member to said needle hub.

18. The device of claim 17 wherein said means for transferring distal pressure comprises:
a) a pair of spaced apart side pieces, positioned on said needle hub parallel to the axis of said cannula and defining a needle hub slot therebetween;

b) a substantially flat needle hub slot end located between said side pieces to form a distal end for said needle hub slot, said needle hub slot end substantially aligned with the proximal side of said opposed protrusion pieces;

c) a first wall and a second wall in said finger manipulation member, said first wall spaced apart from said second wall to define a finger manipulation member slot, said first wall located distal to said second wall, said first wall spaced from said second wall by approximately the width of said opposed protrusions, said finger manipulation slot for receiving and constraining said opposed protrusions therein, each of said walls having an edge directed in approximately the same direction, said first and said second walls each having an opening formed into each of said walls from each respective said edges, each of said openings in said first and second walls shaped in contour to said needle hub in the area where said first and second walls intersect said needle hub when said opposed protrusions are moved into said finger manipulation slot from the direction of said edges; and, d) a tang extending into said opening in said second wall from opposite said edge of said second wall toward said edge of said second wall, said tang being substantially planar with said second wall and shaped in substantial contour to said needle hub slot, said tang contacting said needle hub slot end when said opposed protrusions are moved into said finger manipulation slot from the direction of said edges so that pressure in the distal direction on said finger manipulation member is transferred to said needle hub by the contact between said tang and said needle hub slot end.

19. The device of claim 11 wherein said opposed protrusions extend away from said needle hub at approximately a right angle to the axis of said cannula.

20. The device of claim 11 wherein said needle hub has a bore extending therethrough, said bore aligned with and connected to said cannula.

21. The device of claim 11 wherein said finger manipulation member has at least one substantially planar face.

22. The device of claim 21 wherein said finger manipulation member is elongated.

23. The device of claim 21 wherein said axis of finger contact is contained in the substantially planar face.

24. The device of claim 11 wherein said finger manipulation member is elongated.

* * * * *